(12) United States Patent
Fierer et al.

(10) Patent No.: US 10,790,050 B2
(45) Date of Patent: Sep. 29, 2020

(54) AGGREGATION SERVERS PROVIDING INFORMATION BASED ON RECORDS FROM A PLURALITY OF DATA PORTALS AND RELATED METHODS AND COMPUTER PROGRAM PRODUCTS

(71) Applicant: Greenlight Health Data Solutions, Inc., Cary, NC (US)

(72) Inventors: Christopher George Fierer, Cary, NC (US); Joseph David Hindsley, Jr., Cary, NC (US); Ryan William Bell, Apex, NC (US); Vikram Natarajan, Cary, NC (US); Steven Joseph Emery, Hillsborough, NC (US)

(73) Assignee: Greenlight Health Data Solutions, Inc., Cary, NC (US)

( * ) Notice: Subject to any disclaimer, the term of this patent is extended or adjusted under 35 U.S.C. 154(b) by 323 days.

(21) Appl. No.: 15/670,038

(22) Filed: Aug. 7, 2017

(65) Prior Publication Data
US 2018/0107794 A1 Apr. 19, 2018

Related U.S. Application Data

(60) Provisional application No. 62/409,610, filed on Oct. 18, 2016.

(51) Int. Cl.
| | |
|---|---|
| *G16H 10/60* | (2018.01) |
| *G06F 16/951* | (2019.01) |
| *G16H 15/00* | (2018.01) |
| *G16H 80/00* | (2018.01) |

(52) U.S. Cl.
CPC .......... *G16H 10/60* (2018.01); *G06F 16/951* (2019.01); *G16H 15/00* (2018.01); *G16H 80/00* (2018.01)

(58) Field of Classification Search
CPC ........ G16H 10/60; G16H 80/00; G16H 15/00; G06F 16/951
See application file for complete search history.

(56) References Cited

U.S. PATENT DOCUMENTS

| | | |
|---|---|---|
| 5,772,585 A | 6/1998 | Lavin et al. |
| 7,333,917 B2 | 2/2008 | Greis et al. |
| 7,657,496 B2 | 2/2010 | Aparicio, IV |
| 7,689,441 B1 | 3/2010 | Craft |
| 8,160,981 B2 | 4/2012 | Aparicio, IV |
| 8,249,895 B2 | 8/2012 | Faulkner et al. |

(Continued)

*Primary Examiner* — Christopher L Gilligan
(74) *Attorney, Agent, or Firm* — Sage Patent Group

(57) ABSTRACT

A method in an aggregation server may provide healthcare information based on electronic healthcare records from a plurality of data portals. A master record may be provided in a database, and the master record may include an aggregation of healthcare information for a user based on initial electronic healthcare records received by the aggregation server over a network from a plurality of data portals. A schedule to update the master record for the user may be determined, and the schedule may be based on information included in the master record for the user. The master record in the database for the user may be updated based on current electronic healthcare records received at the aggregation server over the network from at least one of the plurality of data portals, with the master record being updated according to the schedule. Related servers and computer program products are also discussed.

26 Claims, 5 Drawing Sheets

(56) References Cited

U.S. PATENT DOCUMENTS

| | | |
|---|---|---|
| 8,326,865 B2 | 12/2012 | Dettinger et al. |
| 8,352,488 B2 | 1/2013 | Fleming et al. |
| 8,374,891 B2 | 2/2013 | Lassetter et al. |
| 8,555,359 B2 | 10/2013 | Manohar et al. |
| 8,655,783 B1 | 2/2014 | Williams et al. |
| 8,683,316 B2 | 3/2014 | Rangarajan et al. |
| 8,725,603 B1 | 5/2014 | Harman et al. |
| 8,768,801 B1 | 7/2014 | Cheatham |
| 8,768,833 B2 | 7/2014 | Freishtat et al. |
| 8,769,133 B2 | 7/2014 | Hayward |
| 8,769,432 B1 | 7/2014 | Rhyne et al. |
| 8,799,066 B1 | 8/2014 | Nesladek et al. |
| 8,799,124 B1 | 8/2014 | Daken et al. |
| 8,855,377 B1 | 10/2014 | Madhani |
| 8,856,176 B1 | 10/2014 | Venu et al. |
| 8,924,238 B1 | 12/2014 | Nidy et al. |
| 8,924,393 B1 | 12/2014 | Channakeshava |
| 8,930,205 B1 | 1/2015 | Klieman |
| 8,952,898 B1 | 2/2015 | Schaefer |
| 9,076,182 B2 | 7/2015 | Chourasia et al. |
| 9,116,763 B2 | 8/2015 | Kumar et al. |
| 9,129,268 B2 | 9/2015 | Hazlehurst |
| 9,152,693 B1 | 10/2015 | Magdalin |
| 9,213,967 B1 | 12/2015 | Ferguson |
| 9,240,003 B1 | 1/2016 | Vu |
| 2004/0078236 A1 | 4/2004 | Stoodley et al. |
| 2005/0171818 A1 | 8/2005 | McLaughlin |
| 2007/0016450 A1 | 1/2007 | Bhora et al. |
| 2007/0219822 A1 | 9/2007 | Godwin et al. |
| 2008/0052127 A1* | 2/2008 | Rosenfeld ............ G06Q 10/10 705/3 |
| 2012/0191473 A1 | 7/2012 | Severin |
| 2013/0110553 A1* | 5/2013 | Navani ................ G06Q 10/06 705/3 |
| 2013/0297341 A1 | 11/2013 | Safranek |
| 2014/0136233 A1 | 5/2014 | Atkinson et al. |
| 2014/0164003 A1* | 6/2014 | Thesman ............. G06Q 50/22 705/2 |
| 2014/0249859 A1 | 9/2014 | Lorsch |
| 2014/0330925 A1* | 11/2014 | Lee ........................ H04W 4/08 709/217 |
| 2015/0294069 A1 | 10/2015 | Shah |
| 2015/0379198 A1 | 12/2015 | Tambasco, Jr. |
| 2015/0379204 A1 | 12/2015 | Douglass |
| 2016/0042483 A1 | 2/2016 | Vo et al. |
| 2016/0085914 A1 | 3/2016 | Douglass et al. |
| 2016/0098525 A1 | 4/2016 | Maheshwari et al. |
| 2017/0039324 A1* | 2/2017 | Francois ............... G16H 50/30 |
| 2017/0142191 A1* | 5/2017 | Caldwell ............... H04L 67/20 |
| 2017/0208041 A1* | 7/2017 | Kho ..................... H04W 12/02 |

* cited by examiner

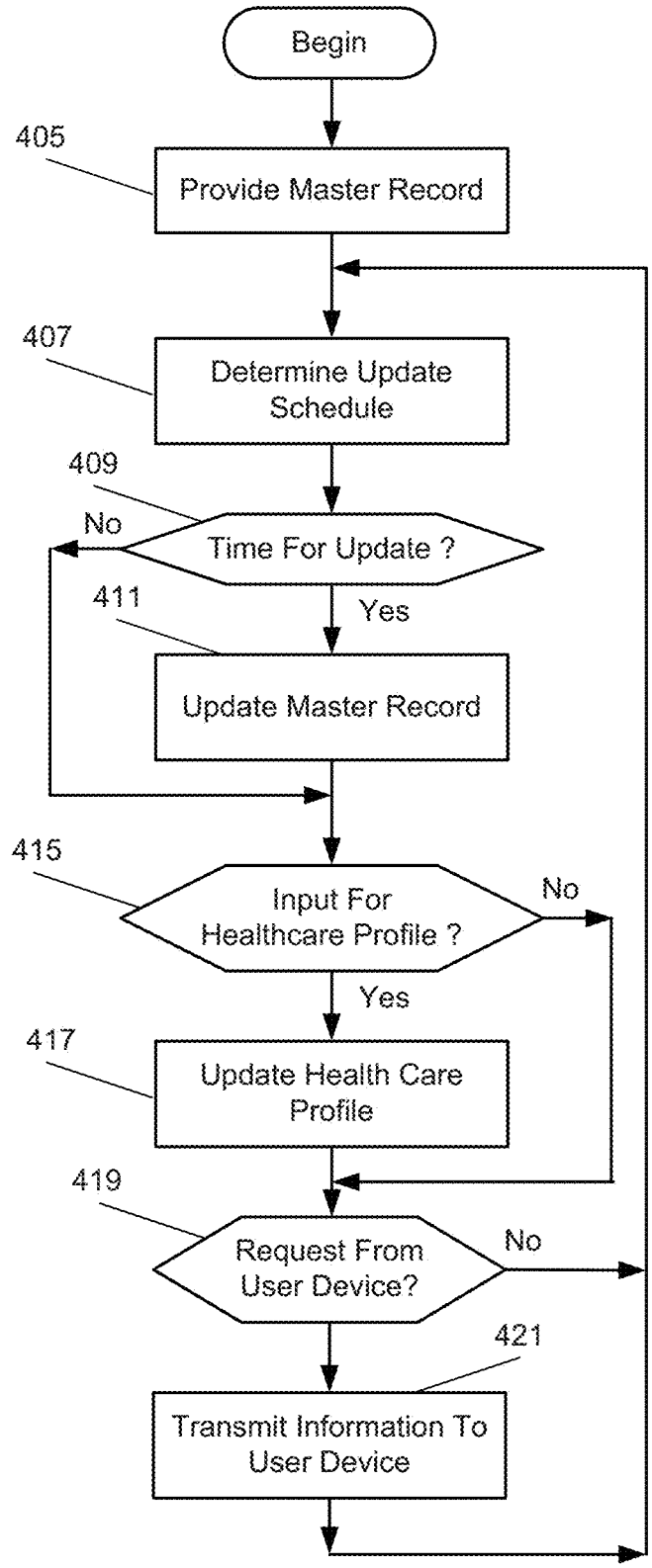

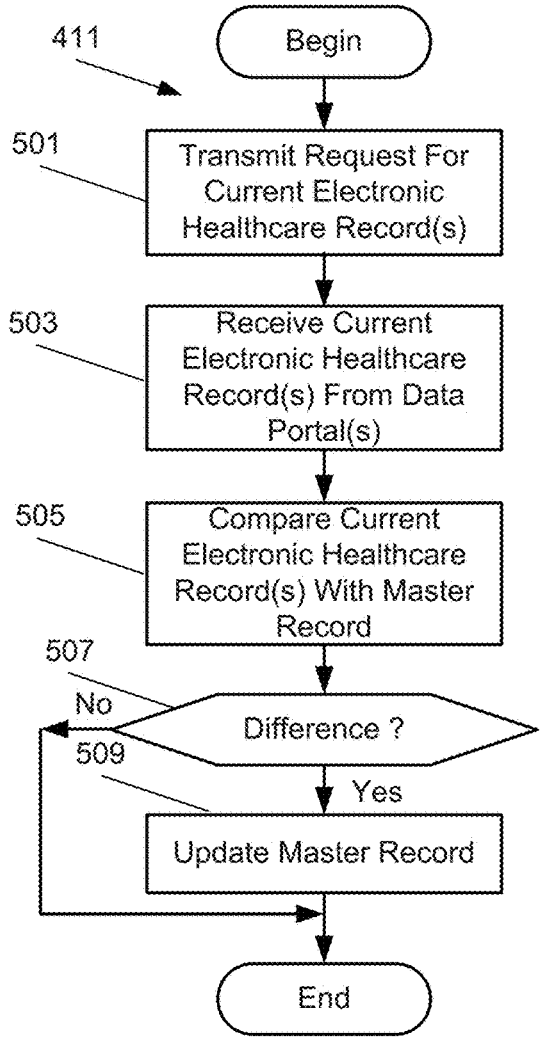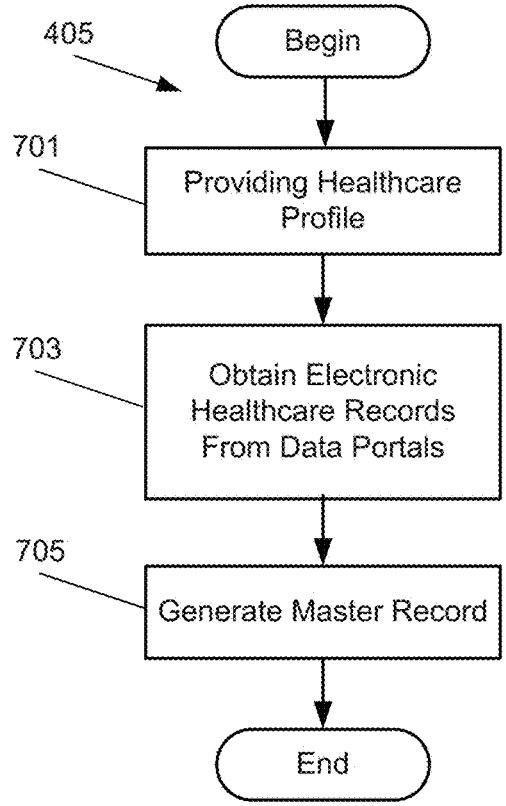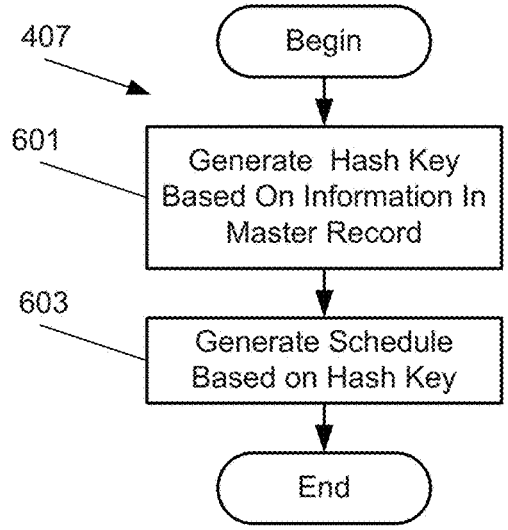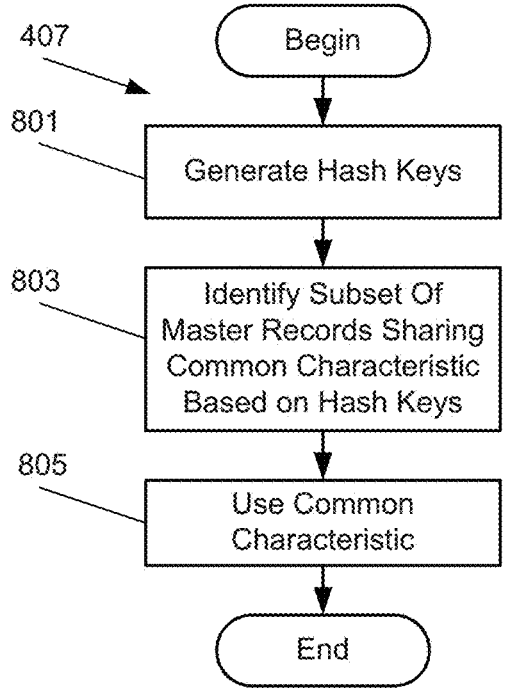

AGGREGATION SERVERS PROVIDING INFORMATION BASED ON RECORDS FROM A PLURALITY OF DATA PORTALS AND RELATED METHODS AND COMPUTER PROGRAM PRODUCTS

RELATED APPLICATION

The present application claims the benefit of priority from U.S. Provisional Application No. 62/409,610, filed Oct. 18, 2017, the disclosure of which is hereby incorporated herein in its entirety by reference.

TECHNICAL FIELD

The present application generally relates to the field of computer systems, and more particularly, to computer systems providing network communication with data portals.

BACKGROUND

Medical service providers (e.g., doctors' offices, hospitals, labs, pharmacies, etc.) use data portals DPs (also referred to as patient portals or patient data portals) to provide patient access to a patient's electronic healthcare records (also referred to as medical data, or personal health records PHRs). Each patient data portal may thus provide a secure online website allowing 24/7 access to the electronic healthcare records (EHRs), which may include personal health information, such as, future/past appointments, lab/test results, prescribed medications, prescription refill dates, immunizations, allergies, conditions, visit summaries, etc. A patient can thus use a personal electronic device PED (e.g., a tablet computer, a laptop computer, a desktop computer, a smartphone, etc.) to remotely and securely acquire his/her electronic healthcare records from one or more medical service providers over a network (such as the Internet) using the respective patient data portals.

Each medical service provider may operate its patient data portal independently, and different medical service providers may use different systems/standards (provided by different vendors) for their respective patient data portals. Moreover, each user may be required to use different access credentials (e.g., usernames and passwords) for each medical service provider from which electronic healthcare records are to be obtained.

SUMMARY

According to some embodiments of inventive concepts, a method in an aggregation server may provide healthcare information based on electronic healthcare records from a plurality of data portals. A master record may be provided in a database, and the master record may include an aggregation of healthcare information for a user based on initial electronic healthcare records received by the aggregation server over a network from a plurality of data portals. A schedule to update the master record for the user may be determined, and the schedule may be based on information included in the master record for the user. The master record in the database for the user may be updated based on current electronic healthcare records received at the aggregation server over the network from at least one of the plurality of data portals, with the master record being updated according to the schedule.

According to some other embodiments of inventive concepts, an aggregation server may provide healthcare information based on electronic healthcare records from a plurality of data portals. The aggregation server may include a network interface configured to provide communication over a network with a plurality of data portals and/or with a plurality of user devices, a processor coupled to the network interface, and a memory coupled to the processor. The memory may store program code that when executed by the processor causes the processor to perform the following operations. A master record may be provided in a database wherein the master record includes an aggregation of healthcare information for a user based on initial electronic healthcare records received by the aggregation server over a network through the network interface from a plurality of data portals. A schedule to update the master record for the user may be determined wherein the schedule is based on information included in the master record for the user. The master record in the database for the user may be updated based on current electronic healthcare records received at the aggregation server over the network through the network interface from at least one of the plurality of data portals. Moreover, the master record may be updated according to the schedule.

According to still other embodiments of inventive concepts, a computer program product may include a non-transitory computer readable storage medium storing program code to provide healthcare information based on electronic healthcare records from a plurality of data portals over a network. The program code when executed by a processor may cause the processor to: provide a master record in a database wherein the master record includes an aggregation of healthcare information for a user based on initial electronic healthcare records received by the aggregation server over a network from a plurality of data portals; determine a schedule to update the master record for the user, with the schedule being based on information included in the master record for the user; and update the master record in the database for the user based on current electronic healthcare records received at the aggregation server over the network from at least one of the plurality of data portals, with the master record being updated according to the schedule.

BRIEF DESCRIPTION OF THE DRAWINGS

The accompanying drawings, which are included to provide a further understanding of the disclosure and are incorporated in and constitute a part of this application, illustrate certain non-limiting embodiments of inventive concepts. In the drawings:

FIGS. 4-8 are flow charts illustrating operations of the processor of FIG. 3 according to some embodiments of inventive concepts;

DESCRIPTION

In the following detailed description, numerous specific details are set forth in order to provide a thorough understanding of embodiments of the present disclosure. However, it will be understood by those skilled in the art that present inventive concepts may be practiced without these specific details. In other instances, well-known methods, procedures, components and circuits have not been described in detail so as not to obscure the present disclosure. It is intended that all embodiments disclosed herein can be implemented separately or combined in any way and/or combination.

Figure 1:
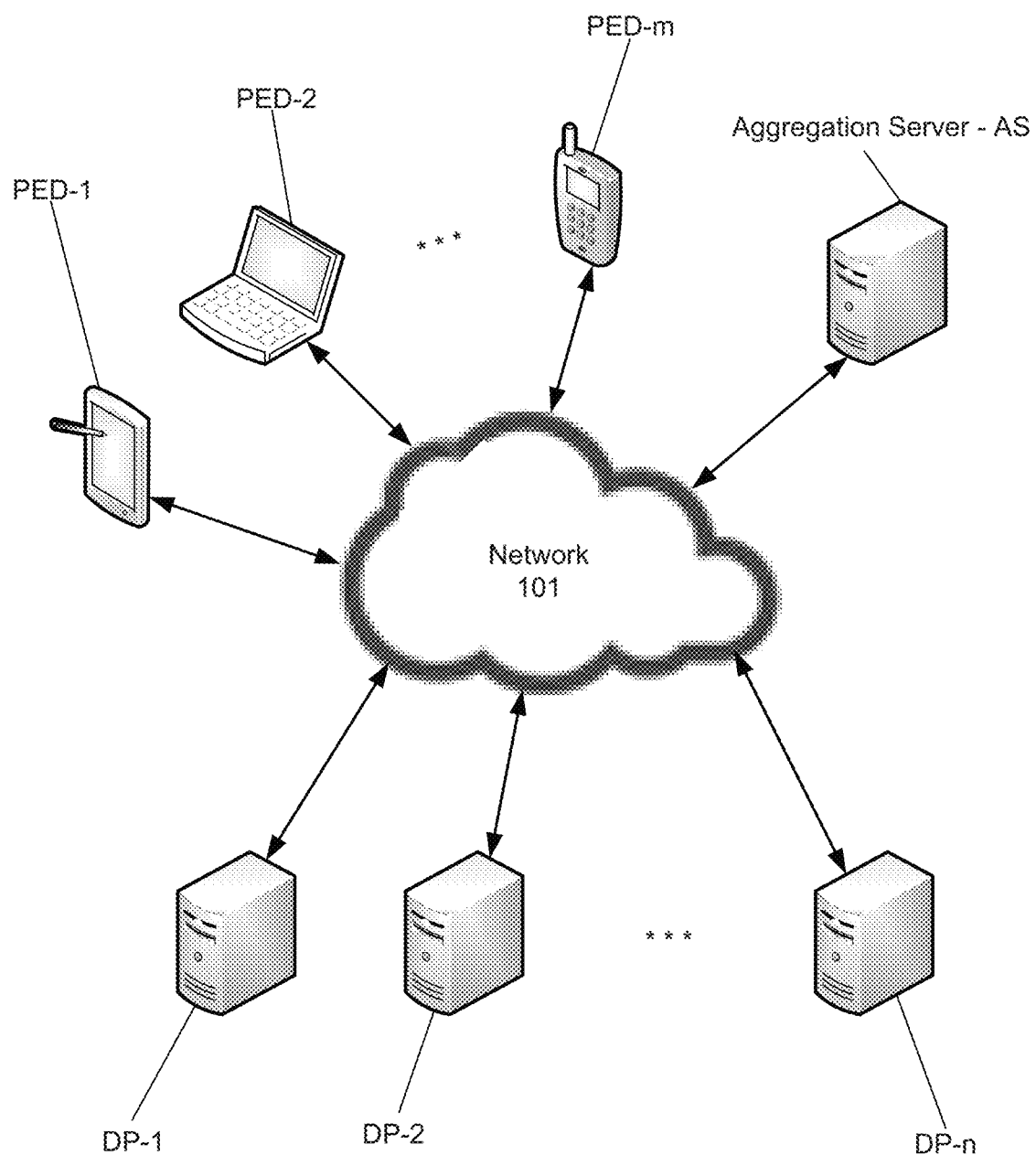
FIG. 1 is a block diagram illustrating an aggregation server in communication with personal electronic devices and data portals according to some embodiments of inventive concepts.

According to some embodiments of inventive concepts illustrated in FIG. 1, an aggregation server AS may aggregate electronic healthcare records from a plurality of patient data portals DP-1 to DP-n for a plurality of patient users, and each patient user may access the aggregated data from the aggregation server AS using a respective personal electronic device PED-1 to PED-m.

Figure 2:
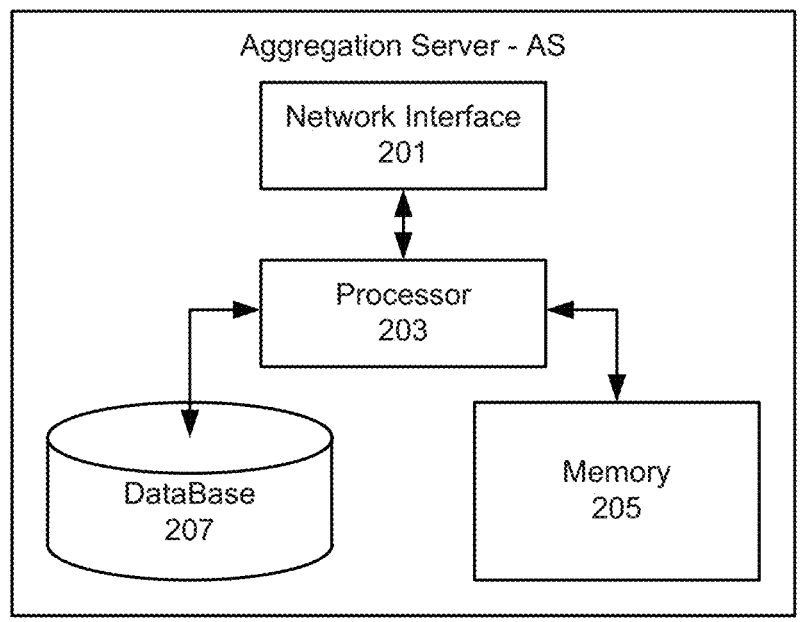
FIG. 2 is a block diagram illustrating elements of application server AS of FIG. 1 according to some embodiments of inventive concepts.

FIG. 2 is a block diagram illustrating elements of application server AS of FIG. 1 according to some embodiments of inventive concepts. As shown, application server AS may include: network interface 201 (also referred to as a network interface circuit) configured to provide network communications over network 101 with personal electronic devices PED-1 to PED-m and patient data portals DP-1 to DP-n; processor 203 (also referred to as a processor circuit) coupled with network interface 201; memory 205 (also referred to as a memory circuit) coupled with processor 203; and database 207 (also referred to as a database circuit) coupled with processor 203. Memory circuit 205 may include computer readable program code that when executed by processor 203 causes processor 203 to perform operations according to embodiments disclosed herein. According to other embodiments, processor 203 may be defined to include memory so that memory 205 is not separately provided.

Figure 3:
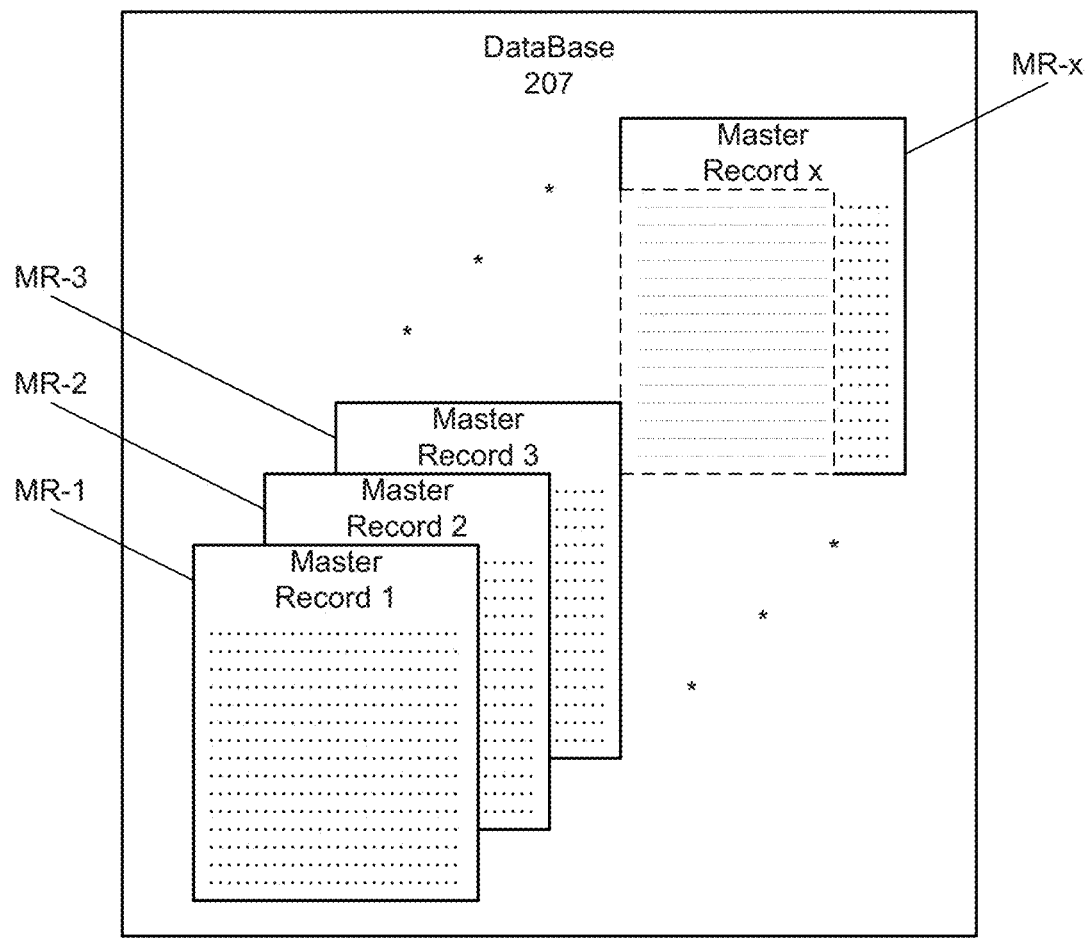
FIG. 3 is a diagram illustrating a database of FIG. 2 storing master records according to some embodiments of inventive concepts.

FIG. 3 is a diagram illustrating database 207 of FIG. 2 storing master records MR-1 to MR-x according to some embodiments of inventive concepts. As discussed herein, a separate master record MR may be provided for each patient user. Moreover, processor 203 and/or memory 205 may be defined to include database 207 so that database 207 is not separately provided.

As discussed in greater detail below, processor 203 may perform operations according to inventive concepts to save/update master records MRs of database 207 for respective user patients. When updating a master record MR of database 207, for example, processor 203 may transmit a request/requests through network interface 201 over network 101 to one or more patient data portals DPs, and processor 203 may receive current healthcare records from the one or more patient data portals DPs through network interface 201. Moreover, processor 203 may receive a request from a personal electronic device PED through network interface 201, and responsive to receiving such a request, processor 203 may transmit requested information from database 207 through network interface 201 to the requesting PED. Operations of application server AS discussed below may thus be performed by processor 203 in cooperation with network interface 201, memory 205, and/or database 207.

For example, a user of personal electronic device PED-1 may establish an account with the aggregation server AS over the network 101. In establishing the account, the user may provide an identification of each medical service provider patient data portal DP from which electronic healthcare records are to be aggregated. For example, the user may identify patient data portals for a primary care physician, one or more specialist physicians (e.g., one or more of an allergist, an oncologist, a cardiologist, a neurologist, a urologist, etc.), a pharmacy, a hospital, etc. For each patient data portal DP identified for the account, the user also provides access (login) credentials (e.g., username and password). Processor 203 may thus receive the listing of patient data portals and respective access credentials through network interface 201. The listing of patient data portals and respective access credentials for a user account may be referred to as a healthcare profile, and processor 203 may save the healthcare profile in a respective master record MR-1 for the patient user of personal electronic device PED-1.

For each patient data portal DP of the healthcare profile of the user account (of the respective master record MR), aggregation server AS processor 203 uses the respective access credentials to connect with associated patient data portals DPs through transceiver 201 and import the associated electronic healthcare records into the user account master record MR. For a given user account for a given user, aggregation server AS processor 203 may thus provide a Master Record MR (also referred to as a Master Patient Record MPR, Longitudinal Care Record LCR, a Longitudinal Health Record LHR, a Living Document, or a Living Record) which is an aggregation of information from the electronic healthcare records from the patient data portals DPs identified in the healthcare profile of the master record MR for the user. The Master Record for a user may thus include personal health information (such as future/past appointments, lab/test results, prescribed medications, prescription refill dates, immunizations, allergies, conditions, visit summaries, etc.) imported from the respective patient data portals DPs of the different medical service providers. The Master Record MR for a user may also be defined to include the healthcare profile for that user, for example, including general information for the patient user (e.g., birth date, age, gender, contact information, ethnicity, etc.), the listing of patient data portals, respective access credentials for the patient data portals, etc.

After initially generating the Master Record MR for a patient user, aggregation server AS processor 203 may establish an account specific schedule to update the Master Record MR based on information in the healthcare profile and/or elements of the personal health information received from the patient data portals. The scheduling may be based on one or more of the following:

Age of the patient user;
A number/frequency of historic appointments with one or more medical service providers;
A scheduled (future) appointment with a medical service provider;
A health condition (e.g., pregnancy, diabetic, cancer, coronary artery disease, etc.);
A prescribed medication;
A prescription refill date;
A frequency of allergy shots;
A lab result;
A type of doctor; and/or
An Insurance type.

As a base line, for example, aggregation server AS processor 203 may update the master record MR for a user account once every 7 days (i.e., once a week). During an update, aggregation server AS processor 203 may reconnect (through network interface 201) with each patient data portal DP of the user account, detect any changes in data for the user, and update the Master Record MR in database 207 accordingly. Based on information discussed above (e.g., personal health information and/or the healthcare profile), however, the frequency of updates may be increased/reduced and/or one off updates may be scheduled.

Regarding Age of the patient user, the update frequency may be increased (e.g., to twice a week) for patents below a threshold age (e.g., for children under 5 years old) and/or for patients above a threshold age (e.g., for adults over 60 years old).

Regarding historic (e.g., past) appointments, the update frequency may be increased (e.g., to twice a week) if the user had more than a threshold number of doctor appointments (e.g., 3 appointments) over a defined period of time (e.g., over the preceding 3 months).

Regarding a scheduled appointment, a single update may be scheduled for a defined period of time (e.g., 48 hours or 72 hours) after the scheduled appointment.

Regarding particular health conditions, the update frequency may be increased (e.g., to twice a week) if the user has a particular health condition (e.g., pregnancy, diabetes, cancer, coronary artery disease, etc.). Similarly, the update frequency may be increased for certain prescribed medications (e.g., insulin, statin drugs, etc.) that may be indicative of a particular health condition.

Regarding a prescription refill date, a single (one off) update may be scheduled to follow the refill date (e.g., by 48 hours or 72 hours).

Regarding a frequency of allergy shots, the update frequency may be increased if the frequency of allergy shots is greater than one shot per month.

Regarding lab results, the update frequency may be increased (e.g., to twice a week) if a particular lab result is indicative of a particular health condition. For example, the update frequency may be increased responsive to a cholesterol reading above a threshold (e.g., total cholesterol>200), responsive to a blood sugar reading above a threshold, etc.

Regarding a type of doctor, the update frequency may be increased if a particular type of doctor (e.g., a cardiologist, an oncologist, etc.) included in the healthcare profile is indicative of a particular health condition.

Regarding an insurance type, the update frequency may be increased if the user is a Medicare/Medicaid patient or if the user is uninsured.

Aggregation server processor 203 can thus use information about the user to better schedule updates of the Master Record in database 207 based on information in the healthcare profile and/or personal health information received from the patient data portals DPs. By individually tailoring the update schedules based on individual information, aggregation server processor 203 may more efficiently maintain up-to-date Master Records for different patient users. In general, Master Records MRs may be updated more frequently for patient users who are likely to more actively use the healthcare system (e.g., patient users with chronic/acute health conditions; patient users in demographic groups that are likely to more actively use the healthcare system, such as, young children, senior citizens, medicare/Medicaid users, the uninsured, etc.). Operation of aggregation server and efficiency/performance thereof may thus be improved by reducing unnecessary updates. In addition, efficiency/performance of network and/or data portal operations may be improved by reducing unnecessary updates.

A patient user can thus use a personal electronic device PED to access information of the Master Record from the aggregation server AS over the Internet. For example, an app on a smartphone or tablet computer may be used to retrieve information of the Master Record MR and display the information to the patient user in an organized and meaningful way. The patient user may thus access an aggregation of current personal health information from multiple patient data portals of multiple medical service providers.

Aggregation server processor 203 may generate predictive data pools for pools of patient users using populations of healthcare profiles, schedules (or scheduling), and/or aggregation paths (where an aggregation path defines particular Medical Record Data to be selectively retrieved during a particular update, e.g., just medications, just Lab results, ALL data, etc.). For example, unique hash keys may be generated for each patient user based on data included in the respective master records MRs, and different pools of patient users may be defined based on similarities/differences between the respective hash keys. Similarities between hash keys of different patient users may be used to identify pools of patient users with a similar health condition/conditions (e.g., pregnant women, cancer patients, patients with coronary artery disease, patients with dementia, etc.). Having defined a pool of patient users with a similar health condition (e.g., using hash keys), application server processor 203 may define a master record update schedule that is applied to the pool of patient users over a period of time (e.g., 365 days).

Figure 9:
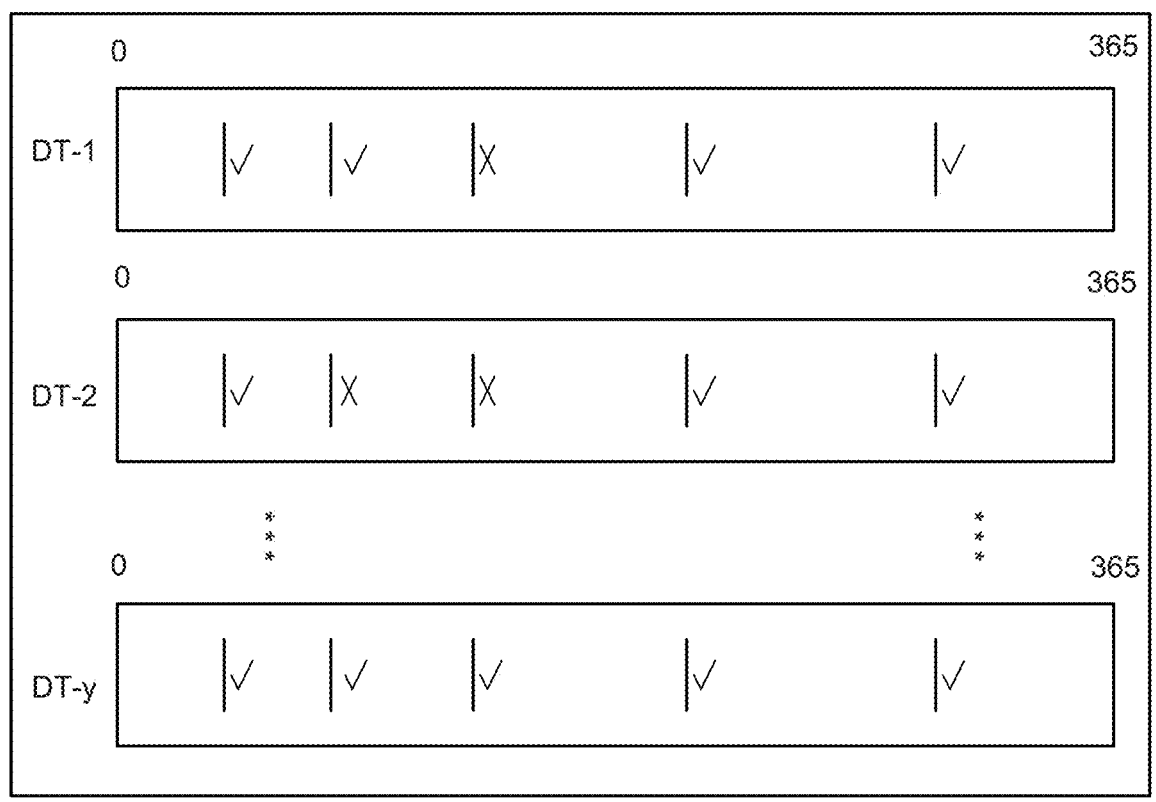
FIG. 9 is a diagram illustrating update results by data type for a schedule of updates according to some embodiments of inventive concepts.

As an example, elements of a patient user hash key may identify patients who are pregnant women, and a schedule of 5 master record updates may be scheduled over time (e.g., over 365 days) for all pregnant women (e.g., following an estimated date of conception as day 0) as illustrated in FIG. 9. At each update for each patient user, application server processor 203 may track whether new data is available (indicated by a check) or not (indicated by an X) for each data type DT (e.g., medications, lab results, data portal, etc.). Based on results from numbers of patient users in the pool over time, application server processor 203 may determine that new data is generally not available for some data types during some of the scheduled updates. As shown in FIG. 9 for one patient user, for example, new data of data type DT-1 was not available during the third scheduled update, and new data of data type DT-2 was not available during the second and third scheduled updates.

Figure 10:
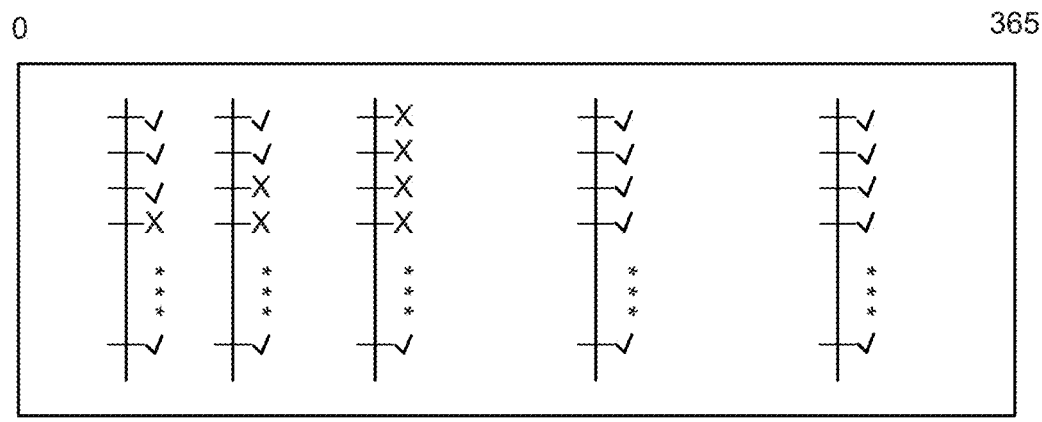
FIG. 10 is a diagram illustrating a schedule of updates and aggregation paths according to some embodiments of inventive concepts.

Based on an aggregation of such data over time for the pool of patient users, application server processor 203 may generate an aggregation path for each scheduled update as shown in FIG. 10. In the example of FIG. 10, the first and second data types may be updated at the first, second, fourth, and fifth scheduled updates for the pool (but not the third scheduled update); the third data type may be updated at the first, fourth and fifth scheduled updates for the pool (but not the second and third scheduled updates); the fourth data type may be updated at the fourth and fifth scheduled updates for the pool (but not the first, second, and third scheduled updates); and the last data type may be updated at all five scheduled updates for the pool. The scheduled updates and aggregation paths of FIG. 10 may be applied to the pool of patient users. Moreover, the scheduled updates and/or aggregation paths of FIG. 10 may change over time based on further aggregation of data for the pool. Moreover, aggregation server processor 203 may use the aggregation of data from the pool of patient users to add/remove scheduled updates and/or to change a time of a scheduled update. Aggregation server AS may thus better predict when to schedule updates for particular pools of patient users and which data type to update during particular scheduled updates.

Given a healthcare Profile for a patient user and known data as referenced against an existing data pool/population, that healthcare profile may be associated with the existing schedule of updates and aggregation paths as illustrated by way of example in FIG. 10. This existing schedule of updates and aggregation paths (also referred to as a schedule) may thus provide predictive scheduling by data type for the pool of patient users having the similar characteristic/characteristics. Moreover, this predictive schedule may be adapted over time as similar patient users are added to the pool.

In addition, a criteria for inclusion in a pool may adapt over time. Patient users who are both pregnant and diabetic, for example, may initially be assigned based on hash keys to two pools (a first pool being a pool for pregnant women, and a second pool being for diabetic patients), and a first update schedule for pregnant women and a second update schedule for diabetic patients may be applied for such women. Over time, aggregation server processor 203 may accumulate enough data to determine that pregnant women who are diabetic should be assigned to a new pool with a different schedule of updates, so that; pregnant women (without diabetes) are assigned to a first pool with a first schedule; diabetic patients (who are not pregnant) are assigned to a second pool with a second schedule; and pregnant women with diabetes are assigned to a third pool with a third schedule (the new pool with the new schedule).

As discussed above, processor 203 may use a patient user hash key to include a patient user in a pool of patient users, for example, based on a particular health condition, and processor 203 may apply an update schedule and aggregation path for that pool to that patient user. Moreover, processor 203 may use the patient user hash key to include a patient user in multiple pools of patient users, for example, based on multiple health conditions, and update schedules and respective aggregation paths for each pool may be applied to that patient user. For a patient user with both coronary artery disease and dementia, for example, aggregation server processor 203 may apply one update schedule and aggregation path triggered by a procedure relating to the coronary artery disease and another update schedule and aggregation path triggered by a diagnosis of dementia.

FIGS. 4-8 are flow charts illustrating operations of the processor of FIG. 3 according to some embodiments of inventive concepts.

FIG. 4 illustrates operations of processor 203 of aggregation server AS providing healthcare information based on electronic healthcare records from a plurality of data portals DPs. At block 405, processor 203 may provide master record MR-1 in database 207, with master record MR-1 including an aggregation of healthcare information for a user based on initial electronic healthcare records received by processor 203 over a network 101 from a plurality of data portals DP-1 to DP-n through network interface 201. More generally, processor 203 may provide a plurality of master records MRs for a plurality of users based on electronic healthcare records received from data portals DPs.

At block 407, processor 203 may determine a schedule to update master record MR-1 for the user, with the schedule being based on information included in master record MR-1 for the user. With a plurality of master records MRs for a respective plurality of users, processor 203 may determine respective schedules to update each of the master records based on information included in the respective master records.

At block 409, processor 203 may determine whether master record MR-1 is scheduled for an update in accordance with the schedule determined at block 407. Responsive to determining that master record MR-1 is scheduled for an update at block 409, processor 203 may update master record MR-1 in data base 207 for the user at block 411 based on current electronic healthcare records received at processor 203 through network interface 201 over network 101 from at least one of the plurality of data portals DPs. Based on decision block 409, processor 203 may update master record MR-1 at scheduled times according to the schedule determined at block 407. Processor 203 may perform operations of blocks 409 and 411 independently for each master record in database 207 according to the respective update schedule determined for each master record.

At block 415, processor 203 may determine if new/different input is received for the healthcare profile of master record MR-1. A user, for example, may start seeing a new doctor, and the user may thus provide identification of a new data portal and respective access credentials through personal electronic device PED-1. The identification and access credentials may be transmitted from personal electronic device PED-1 over network 101 through network interface 201 to processor 203. Responsive to receiving such information at block 415, processor 203 may update the user's healthcare profile in master record MR-1 so that information from the new doctor is included in future master record updates at block 411.

At block 419, processor 203 determines whether a request for healthcare information is received from personal electronic device PED-1. Responsive to receiving such a request from personal electronic device PED-1 through network interface 201 at block 419, processor 203 may transmit (421) information from master record MR-1 through network interface 201 over network 101 to the user device PED-1.

Operations of FIG. 4 may be repeated indefinitely for master record MR-1, with any number of master record updates at blocks 409 and 411, with any number of healthcare profile updates at blocks 417 and 419, and with any number of user requested information transmissions at blocks 419 and 421. As further indicated by the loop back to block 407, the update schedule for master record MR-1 may change over time, for example, based on a changing medical condition of the respective user, based on an aggregation of information from a pool of users, based on a change in a pool of uses with which master record MR-1 is associated, etc. Moreover, processor 203 may perform operations of FIG. 4 separately with respect to each master record included in database 207.

Updating master record MR-1 at block 411 may be performed using operations of FIG. 5. At block 501, processor 203 may transmit a request through network interface 201 to one (or more) of the plurality of data portals DPs, with the request being transmitted according to the schedule and with the request including access credentials allowing access to electronic healthcare records from the one (or more) of the data portals DPs for the user. After transmitting the request at block 501, processor 203 may receive current electronic healthcare records from the one (or more) of the plurality of data portals DPs for the user through network interface 201 at block 503. At block 505, processor may compare the current electronic healthcare records with the healthcare information of master record MR-1 for the user, and at block 509, processor 203 may update master record MR-1 for the user based on differences between the current electronic healthcare records and the healthcare information of the master record. If there are no differences, no update of master record MR-1 may be performed.

The aggregation of healthcare records of master record MR-1 for the user may include a plurality of data types DT-1 to DT-y, and determining the schedule at block 407 may include determining the schedule to include a first update at a first time for a first data type DT-1 and a second data type DT-2 and to include a second update at a second time for the first data type DT-1 and not the second data type DT-2. Stated in other words, different aggregation paths may be provided for different updates. An example of updating the master record at block 411 according to such a schedule with different aggregation paths is shown in FIG. 5.

Responsive to determining that it is time for the first scheduled update at block 409, processor 203 may update master record MR-1 at block 411 by transmitting a first request for current electronic healthcare information of the first data type DT-1 and the second data type DT-2 through network interface 201 to at least one of the plurality of data portals at the first time at block 501, and by receiving current electronic healthcare records of the first data type DT-1 and the second data type DT-2 responsive to the first request through network interface 201 at block 503. At block 505, processor may compare the current electronic healthcare records of the first and second types with healthcare information of the master record for the user, and at blocks 507 and 509, processor 203 may update master record MR-1 based on differences between the current electronic healthcare records and the healthcare information of master record MR-1. If there is no different at block 507, no update is required at block 509.

Responsive to determining that it is time for the second scheduled update at block 409, processor 203 may update master record MR-1 at block 411 by transmitting a second request for current electronic healthcare information of the first data type DT-1 (and not the second data type DT-2) through network interface 201 to at least one of the plurality of data portals at the second time at block 501, and by receiving current electronic healthcare records of the first data type DT-1 responsive to the second request through network interface 201 at block 503. At block 505, processor may compare the current electronic healthcare records of the first type with healthcare information of master record MR-1 for the user, and at blocks 507 and 509, processor 203 may update master record MR-1 based on differences between the current electronic healthcare records and the healthcare information of master record MR-1. If there is no different at block 507, no update is required at block 509.

For example, electronic healthcare information of the first data type DT-1 may be electronic healthcare information from first data portal DP-1, and electronic healthcare information of the second data type DT-2 may be electronic healthcare information from second data portal DP-2. Accordingly, transmitting the first request may include transmitting the first request to first and second data portals DP-1 and DP-2, and transmitting the second request may include transmitting the second request to first data portal DP-1 and not second data portal DP-2.

According to another example, electronic healthcare information of the first data type DT-1 may include one of medication information, laboratory information, and appointment information, and electronic healthcare information of the second data type DT-2 may include one of medication information, laboratory information, and appointment information different than the electronic health care information of the first data type.

As shown in FIG. 6, determining the schedule to update the master record at block 407 may include processor 201 generating a hash key at block 601 based on information in master record MR-1 and generating the schedule to update the master record at block 603 based on the hash key. As noted above, operations of FIG. 4 may be performed independently for each of the master records MRs of database 207, and a unique hash key may thus be generated for each master record MR. Similarities between hash keys of different master records may thus be used to group master records into pools, and characteristics of master records in a pool may be used to generate a same update schedule that may be used for all master records of that pool.

FIG. 7 illustrates operations of providing master record MR-1 of block 405. For example, processor 203 may provide a healthcare profile of master record MR-1 for the user at block 701. The healthcare profile may include a first identification for a first data portal DP-1, a second identification for a second data portal DP-2, first access credentials allowing access to electronic healthcare records from the first data portal DP-1 for the user, and second access credentials allowing access to electronic healthcare records from the second data portal DP-2 for the user. The healthcare profile may be provided based on information received from the user through personal electronic device PED-1, network 101, and network interface 201. At block 703, processor 203 may obtain electronic healthcare records for the user from first and second data portals DP-1 and DP-1 over the network 101 through network interface 201 using the first and second access credentials. Processor 203, for example, may transmit requests to data portals DP-1 and DP-2 including the respective access credentials, and data portals DP-1 and DP-2 may respond with the electronic health care records. At block 705, processor 203 may generate master record MR-1 including information from the electronic healthcare records from data portals DP-1 and DP-2 obtained using the first and second access credentials. Moreover, updating master record MR-1 at block 411 may include updating master record MR-1 based on current electronic health care records received over network 101 from at least one of first and second data portals DP-1 and DP-2.

Providing master record MR-1 at block 405 may include providing a plurality of master records MRs for a plurality of users, and each of the plurality of master records MRs may include an aggregation of healthcare information for a respective one of the plurality of users. According to such embodiments, determining the schedule at block 407 may include processor 203 generating a plurality of hash keys at block 801 so that a respective one of the hash keys is provided for each of the plurality of master records based on information in the respective master record. At block 803, processor 203 may identify a subset of master records from the plurality of master records in the database 207 based on the plurality of hash keys, and each of the master records of the subset may share a common characteristic, with the subset including the master record for the user. At block 805, processor may use the common characteristic of the subset of master records to determine the schedule for each of the master records of the subset, including master record MR-1. After updating the master record at block 411, processor 203 may determine a second schedule to update master record MR-1 at block 407 responsive to detecting a change in at least one of the subset of the plurality of master records. Responsive to the second schedule, processor 203 may updating the master record MR-1 in database 207 for the user at block 411 according to the second schedule based on current electronic healthcare records received at aggregation server AS over the network.

As discussed above, the schedule may be determined for master record MR-1 based on information included in master record MR-1. For example, processor 203 may generate a hash key based on information included in master record MR-1, and processor 203 may use the hash key to determine the schedule for master record MR-1. According to some embodiments, master record MR-1 may include information regarding an appointment for the user with a medical service provider associated with one of the plurality of data portals DPs, and processor 203 may determine the schedule at block 407 by determining the schedule to include an update of the master record based on the appointment. According to some embodiments, the appointment may be a future appointment for the user with the medical service provider, and processor may determine the schedule at block 407 to include an update of information from a data portal DP associated with the medical service provider to follow the appointment.

According to some embodiments, master record MR-1 may include an age of the user, a health condition of the user, a medication prescribed for the user, a lab result for the user, and/or a type of insurance for the user, and processor 203 may determine the schedule at block 407 to include a frequency of updates for the master record for the user based on the age of the user, the health condition of the user, the medication prescribed for the user, the lab result for the user, and/or the type of insurance for the user. According to some embodiments, master record MR-1 may include a frequency of allergy shots scheduled for the user with a medical service provider, and processor 203 may determining the schedule at block 407 to include a frequency of updates of the master record for the user from a data portal associated with the medical service provider based on the frequency of allergy shots.

Determining the schedule at block 407 may include processor 203 determining a first schedule to update master record MR-1. Responsive to updating master record MR-1, processor 203 may determine a second schedule to update the master record at block 407, with the first and second schedules being different. After determining the second schedule, processor 203 may update master record MR-1 in the database 207 for the user at block 411 based on current electronic healthcare records received at aggregation server AS over the network 101 from at least one of the plurality of data portals, with master record MR-1 being updated according to the second schedule. The schedule may change, for example, based on a change in a health condition, a change of doctor, a change of medication, etc.

Providing master record MR-1 at block 405 may include providing a plurality of master records for a plurality of users in database 207, and each of the plurality of master records may include an aggregation of healthcare information for a respective one of the plurality of users. Moreover, determining the update schedule at block 407 may include identifying a first subset of the plurality of master records (e.g., using hash keys and/or common characteristics) including master record MR-1, and determining the schedule to update the first subset of the plurality of master records including master record MR-1. Moreover, processor 203 may identify a second subset of the plurality of master records, determine a second schedule to update the second subset of the plurality of master records, and update a master record of the second subset according to the second schedule. Accordingly, different subsets (groups) of master records may be defined (e.g., based on hash keys and/or common characteristics), and respective update schedules may be provide for the different subsets.

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented in entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

It is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block(s) may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprise," "comprising," "include," "including," "have," "has," "having," or variants thereof when used in this specification, specify the presence of stated features, integers, steps, operations, elements, and/or components, but do not preclude the presence or addition of one or more other features, integers, steps, operations, elements, components, and/or groups thereof. Moreover, when and element/operation is referred to as being "connected," "coupled," "responsive to," or variants thereof to another element/operation, it can be directly connected, coupled, or responsive to the other element/operation, or one or more intervening elements/operations may be present. In contrast, when an element/operation is referred to as being "directly connected," "directly coupled," "directly responsive to," or variants thereof as used herein, there are no intervening elements/operations present.

As used herein, the term "and/or" (abbreviated "/") includes any and all combinations of one or more of the associated listed items Like reference numbers signify like elements throughout the description of the figures.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

That which is claimed is:

1. A method in an aggregation server to provide healthcare information based on electronic healthcare records from a plurality of data portals, the method comprising:
   providing a master patient record in a database wherein the master patient record comprises an aggregation of healthcare information for a patient user based on initial electronic healthcare records received by the aggregation server over a network from a plurality of data portals, wherein the master patient record includes at least one of an age of the patient user, a health condition of the patient user, a medication prescribed for the patient user, a lab result for the patient user, and/or a type of insurance for the patient user;
   determining a schedule at the aggregation server to update the master patient record for the patient user, wherein the schedule is based on information included in the master patient record in the database for the patient user, and wherein determining the schedule comprises determining the schedule to include a frequency of updates for the master patient record for the patient user based on at least one of the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record; and updating the master patient record in the database for the patient user based on current electronic healthcare records received at the aggregation server over the network from at least one of the plurality of data portals, wherein the master patient record is updated according to the schedule.

2. The method of claim 1 wherein determining the schedule to update the master patient record comprises, generating a hash key based on information in the master patient record, and generating the schedule to update the master patient record based on the hash key.

3. The method of claim 1 wherein the master patient record includes information regarding an appointment for the patient user with a medical service provider associated with one of the plurality of data portals, and wherein determining the schedule comprises determining the schedule to include an update of the master patient record to follow the appointment based on the information regarding the appointment included in the master patient record.

4. The method of claim 3, wherein the appointment comprises a future appointment for the patient user with the medical service provider, and wherein determining the schedule comprises determining the schedule to include an update of information from a data portal associated with the medical service provider to follow the future appointment.

5. The method of claim 1 wherein the master patient record includes a frequency of allergy shots scheduled for the patient user with a medical service provider, and wherein determining the schedule comprises determining the schedule to include a frequency of updates of the master patient record for the patient user from a data portal associated with the medical service provider based on the frequency of allergy shots.

6. The method of claim 1 wherein the aggregation of healthcare records of the master patient record for the patient user includes a plurality of data types, wherein determining the schedule comprises determining the schedule to include a first update at a first time for a first data type and a second data type and to include a second update at a second time for the first data type and not the second data type, and wherein updating the master patient record according to the schedule comprises, transmitting a first request for current electronic healthcare information of the first data type and the second data type to at least one of the plurality of data portals at the first time, receiving current electronic healthcare information of the first data type and the second data type responsive to the first request, transmitting a second request for current electronic healthcare information of the first data type and not the second data type to at least one of the plurality of data portals at the second time, and receiving current electronic healthcare information of the first data type and not the second data type responsive to the second request.

7. The method of claim 6 wherein electronic healthcare information of the first data type comprises electronic healthcare information from a first data portal, wherein electronic healthcare information of the second data type comprises electronic healthcare information from a second data portal, wherein transmitting the first request comprises transmitting the first request to the first and second data portals, and wherein transmitting the second request comprises transmitting the second request to the first data portal and not the second data portal.

8. The method of claim 6 wherein electronic healthcare information of the first data type comprises one of medication information, laboratory information, and appointment information, and wherein electronic healthcare information of the second data type comprises one of medication information, laboratory information, and appointment information different than the electronic health care information of the first data type.

9. The method of claim 1 wherein determining the schedule comprises determining a first schedule to update the master patient record, the method further comprising:

responsive to updating the master patient record for the patient user, determining a second schedule to update the master patient record for the patient user, wherein the first and second schedules are different; and after determining the second schedule, updating the master patient record for the patient user in the database based on current electronic healthcare records received at the aggregation server over the network from at least one of the plurality of data portals, wherein the master patient record for the patient user is updated according to the second schedule.

10. The method of claim 9, wherein determining the second schedule comprises determining the second schedule to update the master patient record responsive to updating the master patient record and detecting a change in medication information for the patient user, laboratory information for the patient user, appointment information for the patient user, and/or age of the patient user.

11. The method of claim 1, wherein providing the master patient record comprises providing a plurality of master patient records for a respective plurality of patient users, wherein each of the plurality of master patient records includes an aggregation of healthcare information for a respective one of the plurality of patient users, the method further comprising:

generating a plurality of hash keys so that a respective one of the hash keys is provided for each of the plurality of master patient records corresponding to the respective one of the plurality of patient users based on information in the respective master patient record; and identifying a subset of the plurality of master patient records based on the plurality of hash keys, wherein determining the schedule comprises determining the schedule to update the subset of the plurality of master patient records, and wherein each of the master patient records of the subset is for a different one of the plurality of patient users.

12. The method of claim 11, wherein the schedule is a first schedule, the method further comprising:

after updating the master patient record, determining a second schedule to update the master patient record responsive to detecting a change in at least one of the subset of the plurality of master patient records; and responsive to the second schedule, updating the master patient record in the database for the patient user according to the second schedule based on current electronic healthcare records received at the aggregation server over the network.

13. The method of claim 1 further comprising:
receiving a request over the network from a patient user device associated with the patient user; and
responsive to receiving the request, transmitting information from the master patient record over the network to the patient user device.

14. The method of claim 1, wherein providing the master patient record comprises,
providing a healthcare profile of the master patient record for the patient user wherein the healthcare profile includes a first identification for a first data portal, a second identification for a second data portal, first access credentials allowing access to electronic healthcare records from the first data portal for the patient user, and second access credentials allowing access to electronic healthcare records from the second data portal for the patient user,
obtaining electronic healthcare records for the patient user from the first and second data portals over the network using the first and second access credentials;
generating the master patient record including information from the electronic healthcare records from the first and second data portals obtained using the first and second access credentials; and
wherein updating the master patient record comprises updating the master patient record based on current electronic health care records received over the network from at least one of the first and second data portals.

15. The method of claim 1 wherein updating the master patient record for the patient user comprises,
transmitting a request to one of the plurality of data portals wherein the request is transmitted according to the schedule and wherein the request includes access credentials allowing access to electronic healthcare records from the one of the data portals for the patient user,
after transmitting the request, receiving the current electronic healthcare records from the one of the plurality of data portals for the patient user,
comparing the current electronic healthcare records with the healthcare information of the master patient record for the patient user, and
updating the master patient record for the patient user based on differences between the current electronic healthcare records and the healthcare information of the master patient record.

16. The method of claim 1, wherein providing the master patient record comprises providing a plurality of master patient records for a plurality of patient users, and wherein each of the plurality of master patient records includes an aggregation of healthcare information for a respective one of the plurality of patient users, the method further comprising:
identifying a first subset of the plurality of master patient records for a first subset of the plurality of patient users, wherein determining the schedule comprises determining the schedule to update the first subset of the plurality of master patient records is based on information included in the first subset of the plurality of master patient records for the first subset of the plurality of patient users;
identifying a second subset of the plurality of master patient records for a second subset of the plurality of patient users;
determining a second schedule to update the second subset of the plurality of master patient records for the second subset of the plurality of patient users, wherein determining the schedule to update the second subset of the plurality of master patient records is based on information included in the second subset of the plurality of master patient records for the second subset of the plurality of patient users, and wherein the first and second schedules are different; and
updating a master patient record of the second subset according to the second schedule.

17. The method of claim 16, further comprising:
generating a plurality of hash keys so that a respective one of the hash keys is provided for each of the plurality of master patient records based on information in the respective master patient record, wherein identifying the first and second subsets of the plurality of master patient records comprises identifying the first and second subsets of the plurality of master patient records based on the plurality of hash keys, wherein the first subset of the plurality of master patient records corresponds to a first pool of multiple patient users with a first similar health condition, wherein the second subset of the plurality of master patient records corresponds to a second pool of multiple patient users with a second similar health condition, and wherein the first and second pools of multiple patient users are different.

18. A method in an aggregation server to provide healthcare information based on electronic healthcare records from a plurality of data portals, the method comprising:
providing a master patient record in a database wherein the master patient record comprises an aggregation of healthcare information for a patient user based on initial electronic healthcare records received by the aggregation server over a network from a plurality of data portals, wherein providing the master patient record comprises providing a plurality of master patient records for a plurality of patient users, wherein each of the plurality of master patient records includes an aggregation of healthcare information for a respective one of the plurality of patient users so that each of the plurality of master patient records is provided for a different one of the plurality of patient users;
determining a schedule at the aggregation server to update the master patient record for the patient user, wherein the schedule is based on information included in the master patient record in the database for the patient user, wherein determining the schedule comprises,
identifying a subset of master patient records from the plurality of master patient records in the database, wherein each of the master patient records of the subset shares a common characteristic, wherein each of the master patient records of the subset is for a different one of the plurality of patient users, and wherein the subset includes the master patient record for the patient user, and
using the common characteristic of the subset of master patient records to determine the schedule; and
updating the master patient record in the database for the patient user based on current electronic healthcare records received at the aggregation server over the network from at least one of the plurality of data portals, wherein the master patient record is updated according to the schedule.

19. The method of claim 18 further comprising:
generating a plurality of hash keys so that a respective one of the hash keys is provided for each of the plurality of master patient records based on information in the respective master patient record;
wherein identifying the subset of master patient records comprises identifying the subset of master patient records based on the plurality of hash keys, wherein each of the master patient records of the subset is for a different one of the plurality of patient users.

20. The method of claim 18 wherein the master patient record includes an age of the patient user, a health condition of the patient user, a medication prescribed for the patient user, a lab result for the patient user, and/or a type of insurance for the patient user, and wherein determining the schedule comprises determining the schedule to include a frequency of updates for the master patient record for the patient user based on the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record.

21. An aggregation server to provide healthcare information based on electronic healthcare records from a plurality of data portals, the aggregation server comprising:
a network interface configured to provide communication over a network with a plurality of data portals and/or with a plurality of patient user devices;
a processor coupled to the network interface; and
a memory coupled to the processor and storing program code that when executed by the processor causes the processor to perform operations comprising:
providing a master patient record in a database wherein the master patient record comprises an aggregation of healthcare information for a patient user based on initial electronic healthcare records received by the aggregation server over a network through the network interface from a plurality of data portals, wherein the master patient record includes at least one of an age of the patient user, a health condition of the patient user, a medication prescribed for the patient user, a lab result for the patient user, and/or a type of insurance for the patient user;
determining a schedule at the processor to update the master patient record for the patient user, wherein the schedule is based on information included in the master patient record in the database for the patient user, wherein determining the schedule comprises determining the schedule to include a frequency of updates for the master patient record for the patient user based on at least one of the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record; and
updating the master patient record in the database for the patient user based on current electronic healthcare records received at the aggregation server over the network through the network interface from at least one of the plurality of data portals, wherein the master patient record is updated according to the schedule.

22. A computer program product comprising a non-transitory computer readable storage medium storing program code to provide healthcare information based on electronic healthcare records from a plurality of data portals over a network, the program code when executed by a processor causes the processor to:
provide a master patient record in a database wherein the master patient record comprises an aggregation of healthcare information for a patient user based on initial electronic healthcare records received by the aggregation server over a network from a plurality of data portals, wherein the master patient record includes at least one of an age of the patient user, a health condition of the patient user, a medication prescribed for the patient user, a lab result for the patient user, and/or a type of insurance for the patient user;
determine a schedule at the aggregation server to update the master patient record for the patient user, wherein the schedule is based on information included in the master patient record in the database for the patient user, wherein determining the schedule comprises determining the schedule to include a frequency of updates for the master patient record for the patient user based on at least one of the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record; and
update the master patient record in the database for the patient user based on current electronic healthcare records received at the aggregation server over the network from at least one of the plurality of data portals, wherein the master patient record is updated according to the schedule.

23. An aggregation server to provide healthcare information based on electronic healthcare records from a plurality of data portals, the aggregation server comprising:
a network interface configured to provide communication over a network with a plurality of data portals and/or with a plurality of patient user devices;
a processor coupled to the network interface; and
a memory coupled to the processor and storing program code that when executed by the processor causes the processor to perform operations comprising:
providing a master patient record in a database wherein the master patient record comprises an aggregation of healthcare information for a patient user based on initial electronic healthcare records received by the aggregation server over a network through the network interface from a plurality of data portals, wherein providing the master patient record comprises providing a plurality of master patient records for a plurality of patient users, and wherein each of the plurality of master patient records includes an aggregation of healthcare information for a respective one of the plurality of patient users;
identifying a first subset of the plurality of master patient records for a first subset of the plurality of patient users;
determining a schedule at the processor to update the master patient record for the patient user, wherein the schedule is based on information included in the master patient record in the database for the patient user, wherein determining the schedule comprises determining the schedule to update the first subset of the plurality of master patient records based on information included in the first subset of the plurality of master patient records for the first subset of the plurality of patient users;

updating the master patient record in the database for the patient user based on current electronic healthcare records received at the aggregation server over the network through the network interface from at least one of the plurality of data portals, wherein the master patient record is updated according to the schedule;

identifying a second subset of the plurality of master patient records for a second subset of the plurality of patient users;

determining a second schedule to update the second subset of the plurality of master patient records for the second subset of the plurality of patient users, wherein determining the schedule to update the second subset of the plurality of master patient records is based on information included in the second subset of the plurality of master patient records for the second subset of the plurality of patient users, and wherein the first and second schedules are different; and updating a master patient record of the second subset according to the second schedule.

24. The aggregation server of claim 23 wherein the master patient record includes an age of the patient user, a health condition of the patient user, a medication prescribed for the patient user, a lab result for the patient user, and/or a type of insurance for the patient user, and wherein determining the schedule comprises determining the schedule to include a frequency of updates for the master patient record for the patient user based on the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record.

25. A computer program product comprising a non-transitory computer readable storage medium storing program code to provide healthcare information based on electronic healthcare records from a plurality of data portals over a network, the program code when executed by a processor causes the processor to:

provide a master patient record in a database wherein the master patient record comprises an aggregation of healthcare information for a patient user based on initial electronic healthcare records received by the aggregation server over a network from a plurality of data portals, wherein providing the master patient record comprises providing a plurality of master patient records for a plurality of patient users, and wherein each of the plurality of master patient records includes an aggregation of healthcare information for a respective one of the plurality of patient users;

identify a first subset of the plurality of master patient records for a first subset of the plurality of patient users;

determine a schedule at the aggregation server to update the master patient record for the patient user, wherein the schedule is based on information included in the master patient record in the database for the patient user, wherein determining the schedule comprises determining the schedule to update the first subset of the plurality of master patient records based on information included in the first subset of the plurality of master patient records for the first subset of the plurality of patient users;

update the master patient record in the database for the patient user based on current electronic healthcare records received at the aggregation server over the network from at least one of the plurality of data portals, wherein the master patient record is updated according to the schedule;

identify a second subset of the plurality of master patient records for a second subset of the plurality of patient users;

determine a second schedule to update the second subset of the plurality of master patient records for the second subset of the plurality of patient users, wherein determining the schedule to update the second subset of the plurality of master patient records is based on information included in the second subset of the plurality of master patient records for the second subset of the plurality of patient users, and wherein the first and second schedules are different; and update a master patient record of the second subset according to the second schedule.

26. The computer program product of claim 25 wherein the master patient record includes an age of the patient user, a health condition of the patient user, a medication prescribed for the patient user, a lab result for the patient user, and/or a type of insurance for the patient user, and wherein determining the schedule comprises determining the schedule to include a frequency of updates for the master patient record for the patient user based on the age of the patient user included in the master patient record, the health condition of the patient user included in the master patient record, the medication prescribed for the patient user included in the master patient record, the lab result for the patient user included in the master patient record, and/or the type of insurance for the patient user included in the master patient record.

* * * * *